United States Patent [19]

Larner et al.

[11] Patent Number: 5,124,360

[45] Date of Patent: Jun. 23, 1992

[54] DIETARY SUPPLEMENT FOR INSULIN-RESISTANT DIABETICS

[75] Inventors: Joseph Larner; Alison Kennington, both of Charlottesville, Va.

[73] Assignee: The University of Virginia Alumni Patents Foundation, Charlottesville, Va.

[21] Appl. No.: 672,778

[22] Filed: Mar. 21, 1991

Related U.S. Application Data

[63] Continuation-in-part of Ser. No. 320,482, Mar. 8, 1989, abandoned.

[51] Int. Cl.⁵ ............................................. A61K 31/045
[52] U.S. Cl. ..................................... 514/738; 514/866
[58] Field of Search ................................ 514/738, 866

[56] References Cited

FOREIGN PATENT DOCUMENTS

3A138126 10/1979 Japan .................................. 514/738

OTHER PUBLICATIONS

Holub, B., "The Nutritional Significance . . . ", Adv. Nutr. Res. 4 107–141 (1982).
Schweizer et al., "Low Molecular . . . ", J. Sci. Agric. 29 148–154 (1978).
Phillips et al., "Cyclitols in Soybean", J. Agric. Food. Chem. 30 456–458 (1982).
Wober et al., "Untersuchungen . . . ", Monatshefte für Chemie 102 459–464 (1971).
Price et al., "Effect of Aldose Reductase . . . ", CA: 109, 71448 (1988).
Knudsen et al., "Myo-Inositol Normalizes Decreased . . . ", CA: 110, 50387 (1989).
Merck Index pp. 722–723, Compound #4861.

*Primary Examiner*—C. Warren Ivy
*Assistant Examiner*—Celia Chang
*Attorney, Agent, or Firm*—Oblon, Spivak, McClelland, Maier & Neustadt

[57] ABSTRACT

A dietary supplement for the therapeutic treatment of those exhibiting clinical symptoms of insulin-resistant type II diabetes, and preventing the development of clinical symptoms in those genetically predisposed to the development of such symptoms, is provided by the administration of a dietary supplement comprising D-chiro-inositol. The dietary supplement is preferably administered orally, in vitamin-like amounts.

4 Claims, No Drawings

DIETARY SUPPLEMENT FOR INSULIN-RESISTANT DIABETICS

This application is a continuation-in-part of application Ser. No. 07/320,482, filed on Mar. 8, 1989, now abandoned.

FIELD OF THE INVENTION

This invention pertains to a supplement for the treatment of symptomatic insulin-resistant diabetes, and intervention to prevent the development of clinical symptoms in those predisposed to the development of insulin-resistant diabetes. Specifically, a dietary supplement comprising D-chiro-inositol is provided.

BACKGROUND OF THE PRIOR ART

As disclosed in copending U.S. Patent application Ser. No. 07/320,484, in the names of Larner, Kennington, Huang and Shen, successful purification, to essential homogeneity, of at least two substances appearing to mediate the activity of insulin, particularly in terms of activation of pyruvate dehydrogenase, as well as the inhibition of other enzyme systems, has been achieved. Structural analysis of the insulin mediator possessing the biological activity of activating pyruvate dehydrogenase (PDH) has surprisingly identified this mediator to be comprised of a glycophosphatidylinositol anchor-type molecule comprising the optically active carbohydrate D-chiro-inositol. Further research as disclosed in U.S. Patent application Ser. No. 07/476,953, inventors Larner, Kennington and Shen, have demonstrated that D-chiro-inositol is either absent, or present in extremely low levels, in type II, insulin-resistant diabetics, in contrast to the levels observed in non-diabetic control individuals As an example, the average concentration of D-chiro-inositol in control non-diabetic individuals is about 900 nanograms per milliliter. The level in type II diabetics is uniformly below about 200 nanograms. On the basis of this distinction, a screening diagnostic has been established, to determine the presence or absence of D-chiro-inositol in the urine and other body fluids. An absence of D-chiro-inositol is evidence of a genetic predisposition for the development of clinical symptoms of type II diabetes, or confirmation of the presence of type II diabetes in those exhibiting some or all of the classical, clinical symptoms.

Further research has indicated that insulin-resistant diabetes may in fact be due to a genetic inability to synthesize, in vivo, D-chiro-inositol, an essential carbohydrate of the insulin mediator responsible for activation of PDH. This chiro sugar is not available in sufficient quantities in conventional diets to compensate for the deficiency in the synthetic pathway necessary to synthesize this compound, and thereby build the insulin mediator. In the absence of the insulin mediator, administration of insulin will not address the symptoms of type II diabetes.

Accordingly, it remains an object of those skilled in the art to find an effective treatment to prevent the development of clinical, symptomatic type II insulin-resistant diabetes in those genetically predisposed to that development, and to intervene in those exhibiting clinical symptoms of type II diabetes.

SUMMARY OF THE INVENTION

The above objects, and others made clear by the specification set forth below are achieved through the provision of a dietary supplement, comprising therapeutic amounts of D-chiro-inositol. This carbohydrate can be isolated from pine needles, where it is present in the methylester form, as well as chick peas, otherwise known as garbanzo beans, and other natural sources. When administered as a vitamin, in appropriate therapeutic amounts, the carbohydrate is absorbed directly through the lining of the gastrointestinal system, and available for utilization in the preparation of the insulin mediator.

DETAILED DESCRIPTION OF THE INVENTION

The essential, non-dietary carbohydrate that is the focus of this invention, D-chiro-inositol, is related to myoinositol, the structures of the various optically active compounds being set forth herein below.

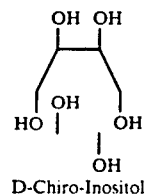
D-Chiro-Inositol

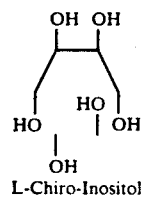
L-Chiro-Inositol

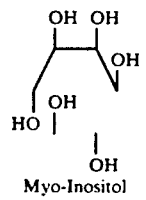
Myo-Inositol

D-chiro-inositol is available from non-dietary sources, in forms not readily assimilated by the body. Thus, the methylester of D-chiro-inositol (DCI) is found in the pine needles of Monterrey pines, indigenous to California. Various esterified forms can also be isolated from chick peas, upon isolated from legumes (Schweizer, T. F., Horman, I., Wuersch, P, 1978, *J. Sci. Food Agric.*, 29, pages 148-154. However, the assimilatable sugar itself does not appear, in sufficient quantities, in normal dietary foods, to make up for a lack of the ability to synthesize the sugar. This inability prevents the formation of an insulin mediator responsible for the activation of PDH. Thus, individuals exhibiting diabetic symptoms as a result of this deficiency, will not respond to treatment with insulin. This is the classic phenotype of the type II or insulin-resistant diabetic. Very little effective therapeutic treatment is available for these individuals.

The provision of a dietary supplement, in vitamin amounts, to provide an in vivo therapeutic level of D-chiro-inositol, overcomes this deficiency. Administration of D-chiro-inositol to those identified, through the screening test discussed above, as genetically predisposed to the development of clinical symptoms of insulin-resistant diabetes, may be employed to prevent the development of these clinical symptoms, as the cause of the insulin-resistance itself, the failure to synthesize the mediator, is avoided. Similarly, those exhibiting clinical symptoms, to the extent they are dependent on the absence of the mediators, may be treated by simple administration of the dietary supplement. Administration of D-chiroinositol to diabetic mammalian models results in the reduction of blood glucose levels. At a minimum, administration of the dietary supplement should remove the insulin resistance, making the diabetic state treatable through conventional insulin therapies.

As noted above, D-chiro-inositol can be isolated from natural sources through purification and deesterification reactions. It can also be synthesized directly from myoinositol, commonly available, by direct inversion of the hydroxyl on the three position.

As noted above, in non-diabetics, and those not likely to develop the diabetic condition, DCI is not present in substantial concentrations. Accordingly, the dietary supplement need be present only in vitamin-like concentrations to provide an adequate means of intervening in clinical insulin-resistant diabetes, as well as preventing the onset of clinical symptoms in those predisposed to their development. In general, dosage values will range from 25 to 100 milligrams per kilogram of body weight, and may be achieved through a variety of pathways. As noted above, the carbohydrate is directly absorbed, and thus may be most conveniently administered orally. Other forms of administration are also suitable.

The active agent, DCI, may be administered alone, or together with other actives. The actives may be combined, by oral administration, with additives chosen from the group consisting of sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium carbon, sodium carbonate, lactose, calcium phosphate or sodium phosphate; granulating and disintegrating agents, such as maize starch, or alginic acid,; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceral distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g. lecithin), a condensation product of an alkylene oxide with a fatty acid (e.g., polyoxyethylene stearate), a condensation product of ethylene oxide with a long chain aliphatic alcohol (e.g., haptadecaethyleneoxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension may also contain one or more preservative such as ethyl or n-propyl p-hydroxybenzoate, one or more coloring agent, one or more flavoring agent, and one or more sweetening agent, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oil suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for the preparation of an aqueous suspension by the addition of water provide the active ingredient in admixture with a dispersing or wetting agent, a suspending agent, and one or more preservative. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, such as a solution in 1,3-butanediol. Among the acceptable vehicles and solvents that may be employed are water.

There are no known toxic or deleterious side effects from the administration of DCI. Due to the very low concentrations at which therapeutic levels are achieved, the DCI can be administered to virtually all those diagnosed either exhibiting clinical symptoms of type II diabetes or genetically predisposed to the development, through the screening test discussed above.

Thus, the dietary additive addressed herein may be administered to infants over the age of one year, and all others at risk or exhibiting clinical symptoms. Under the age of one year, it is believed that the digestive system may be insufficiently developed to achieve positive results through the addition of the dietary supplement.

The invention disclosed above has been described with regard to specific examples, dosage levels, carriers and additives. Within the scope of the claims appended hereto, other formats, variations and combinations will occur to those of ordinary skill in the art, without the exercise of inventive skill. Such alterations do not depart from the invention, except as provided in the claims appended hereto.

What is claimed is:

1. An oral composition of matter effective in the reduction of blood glucose level of a diabetic individual, consisting essentially of D-chiroinositol (DCI) in amounts sufficient to provide a therapeutic level in said individual, to achieve reduction of the blood glucose level upon administration to said individual.

2. The composition of claim 1, wherein said D-chiroinositol is present in amounts between 25 and 100 milligrams.

3. A method for the therapeutic treatment of an individual exhibiting type II, insulin-resistant diabetes, comprising orally administering to said individual an oral composition of matter effective in the reduction of blood glucose levels of a diabetic individual, consisting essentially of DCI, in amounts sufficient to provide a therapeutic level of DCI for reduction of the blood glucose level of said individual.

4. The method of claim 3, wherein said DCI is present in amounts of 25 mg/kg to 100 mg/kg.

* * * * *